United States Patent [19]

Niedrach et al.

[11] Patent Number: 4,627,907
[45] Date of Patent: Dec. 9, 1986

[54] LONG LIFE PORTABLE OXYGEN SENSOR WITH HIGH STABILITY

[75] Inventors: Leonard W. Niedrach, Schenectady; Fritz G. Will, Scotia, both of N.Y.

[73] Assignee: General Electric Company, Schenectady, N.Y.

[21] Appl. No.: 667,934

[22] Filed: Nov. 2, 1984

[51] Int. Cl.[4] ............................................. G01N 27/52
[52] U.S. Cl. .................... 204/415; 204/406; 204/408
[58] Field of Search ............... 204/406, 407, 415, 1 P, 204/408

[56] References Cited

U.S. PATENT DOCUMENTS 3,719,575  3/1973  Niedrach et al. ............... 204/415
3,767,552  10/1973  Lauer ............................ 204/415 X
3,948,746  4/1976  Poole ............................ 204/415 X
4,132,616  1/1979  Tantram et al. ............... 204/415

Primary Examiner—G. L. Kaplan
Attorney, Agent, or Firm—Paul E. Rochford; James C. Davis, Jr.; Paul R. Webb, II

[57] ABSTRACT

An oxygen sensor having increased stability in its sensitivity is provided. The oxygen sensor includes a sensing electrode spaced from a cadmium counter electrode. An alkaline electrolyte extends between the electrodes and permits the formation of cadmium hydroxide in the counter electrode as the cell is used. An electrical circuit connects the counter electrode and sensing electrode externally of the cell. The circuit includes a resistor and thermistor network and a voltmeter. Readings on the voltmeter can be calibrated to show the concentration of ambient oxygen diffusing a polymer membrane to the sensor electrode.

8 Claims, 3 Drawing Figures

LONG LIFE PORTABLE OXYGEN SENSOR WITH HIGH STABILITY

BACKGROUND OF THE INVENTION

The present invention relates to oxygen sensors suitable for use in spacecraft and for other uses. More specifically it relates to oxygen sensors having improved useful life and stability in operation and suitable for use on the space shuttle.

It has been observed that prior art copper-alkalioxygen sensors exhibit a steady decline in oxygen sensitivity with time. Even the most expensive and sophisticated of these portable oxygen sensors must be adjusted continually over their useful life in order to compensate for and offset what has appeared to be a gradual reduction in sensing sensitivity.

It has also been observed that such prior art oxygen sensors have a total life of approximately 8000 hours when exposed to 1 atmosphere of air at 75° F. Total life includes both useful operating life and exposure to oxygen for testing, storage and for any other reason. The calculated total life of a sensor as illustrated in FIG. 1 is approximately 9200 hours. The original specifications of the National Aeronautics and Space Administration for such sensors is 6236 operational hours of useful operating life.

During the time that such a conventional prior art sensor is functioning the sensitivity of the device, that is the voltage produced for a given rate of oxygen absorbed, continually decreases. Adjustment of the sensor is accordingly continually needed.

Because substantial testing and operation of sensors is necessary prior to an actual mission, an appreciable portion of the total life of such a sensor is used up in laboratory testing, in various calibrations and in an air exposure aboard the spacecraft before the scheduled launch. The delay problem can be further extended by delays in the actual launch thus using up a further portion of the total life of the sensor.

Calibration to adjust sensitivity is needed periodically.

Presently oxygen sensors having a total life of about 9000 hours exhibit a gradual decrease in sensitivity and this decrease amounts to approximately 0.5% per month. Such decrease is undesirable and necessitates frequent recalibration and adjustment of circuitry external to the sensor cell itself.

BRIEF STATEMENT OF THE INVENTION

It is one object of the present invention to improve the design of oxygen sensors for space and other applications.

Another object is to provide an oxygen sensor having reduced loss of oxygen sensitivity.

Another object is to provide an oxygen sensor having a useful life which is not marked by loss of a significant level of oxygen sensitivity.

Another object is to provide an oxygen sensor for space applications which has a greater stability in continuous indication of oxygen level.

A further object is to provide a design of an oxygen sensor which has a very low loss of oxygen sensitivity.

Other objects and advantages of the present invention will be, in part, apparent and, in part, pointed out in the description which follows.

In one of its broader aspects, objects of the present invention may be achieved by providing an oxygen sensor of increased stability and having a cadmium counter electrode. The sensor includes a sensor electrode adapted to reduce oxygen which permeates thereto through a diffusion membrane, a counter electrode of porous cadmium, an aqueous alkaline solution, a set of conductors and a resistor network external to the sensor cell and a voltmeter connected in parallel with the resistor network.

BRIEF DESCRIPTION OF THE DRAWINGS

The description which follows will be better understood by reference to the accompanying drawings in which.

DETAILED DESCRIPTION OF THE INVENTION

Figure 1:
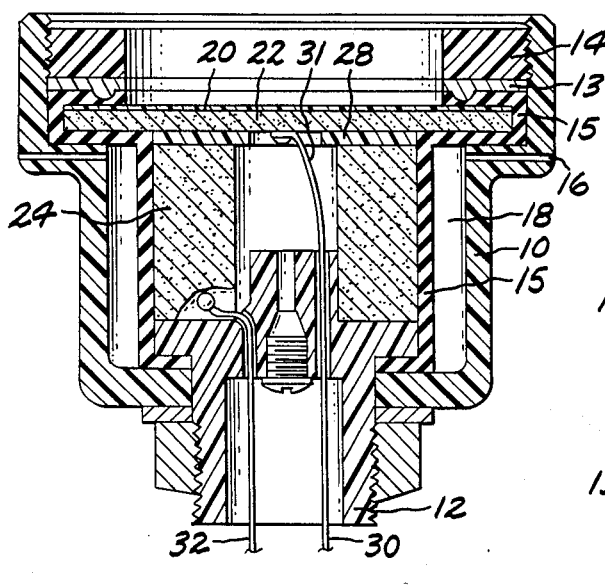
FIG. 1 is an axial sectional view of an oxygen sensor as provided by the prior art.

The sensor of FIG. 1 is a prior art sensor and is essentially a copper-air battery. It includes an outer casing 10, preferably of polymeric material, and having an internally threaded insulating bushing 12 at its lower end and an externally threaded plastic insert 14 at its upper end. Between the bushing 12 and the insert 14 are essential elements of the sensor. An impervious washer 13 is positioned between the upper portion of bladder 15 and insert 14. This holds the top inwardly extending portion of bladder 15 against the outer portions of membrane 20 and defines the area of membrane 20 exposed to the atmosphere. An expansion bladder 15, of neoprene or other suitable rubber such as ethylene propylene rubber, laterally surrounds the essential components of the battery and is positioned between these elements and the housing 10.

The bladder 15 is spaced from the walls of the housing in the lower portion of the housing to permit its lateral expansion and vent holes 16 provide means by which gas pressure is equilibrated in the space 18 between the housing and the bladder and the outside atmosphere. At the upper part of the essential elements of the sensor is a polymer membrane 20. The polymer membrane has the capacity to perfuse and pass oxygen at a rate which is proportional to the partial pressure of oxygen in contact with the exterior surface of the membrane. Oxygen which is in contact with the exterior of the sensor passes through the membrane 20 and into contact with a sensing electrode 22.

The sensing electrode is porous metal and it is gold plated. The function of the gold on the sensing electrode is that of catalyzing the electro-reduction of oxygen. The extent of gold plating must be sufficient to permit effective reduction of the oxygen and this degree of plating to achieve such effective reduction will be apparent to those skilled in the art. The porous sensing electrode makes contact with and has its pores wetted with an aqueous alkaline solution, which may be potassium hydroxide electrolyte, contained within the internal chamber of the sensor where a porous copper counter electrode 24 is located. The copper counter electrode is separated from the sensing electrode 22 by the insulating ring 28.

Figure 3:
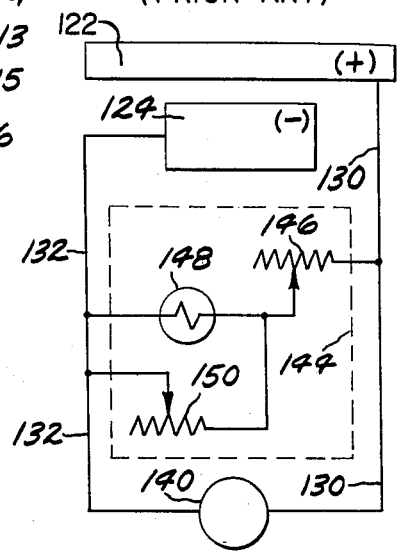
FIG. 3 is a schematic drawing of a sensing circuit as provided in connection with the present invention.

Suitable circuitry such as is illustrated in and described with reference to FIG. 3 is provided between the sensing electrode and the copper counter electrode. This circuitry includes connecting wires 30 and 32, a resistance network and a thermistor to compensate for temperature variations. The circuitry also includes a voltmeter from which readings can be taken of the voltage drop across the network resulting from the current flow between the sensing electrode 20 and the porous copper counter electrode 24. The voltage generated can be calibrated to provide an indication of the partial pressure of oxygen which is in contact with the exterior surface of the polymer membrane 20.

When oxygen diffuses through the polymer membrane and comes in contact with the sensing electrode, wetted with potassium hydroxide electrolyte, it is reduced electrochemically by electrons derived via the external wires and circuitry from the porous copper counter electrode 24 which is concurrently oxidized electrochemically. At constant temperature the rate of these reactions, and hence the associated current flow is proportional to the oxygen partial pressure in the environment being monitored. In this prior art device the sensitivity deteriorates with time and may decrease by about one half percentage point per month. The current causes a potential drop across the resistance network connecting sensing electrode 22 and the porous copper counter electrode 24. The potential drop is measured by a voltmeter connected across the network. Wire 30 is connected through wire 31 to the sensing electrode and wire 32 is connected to the porous copper electrode 24.

The following are a few of the particulars of this prior art structure. The oxygen-diffusing membrane is a composite of fluorinated ethylene propylene polymer (FEP) and tetrafluoro ethylenepolymer (PTFE) membrane. See in this connection U.S. Pat. No. 3,616,411 as to alternative membranes.

The potassium hydroxide solution is a 25 weight % KOH electrolyte. The thickness of the oxygen-permeable membrane is typically about 0.025 mm. The sensing electrode is a disk with a 3.3 cm diameter and a 0.14 cm thickness. The counter electrode is a copper cylinder weighing 7.6 gm and having a center bore. It has an outer diameter of 1.8 cm, an inner diameter of 0.8 cm and a length of 1.2 cm. The spacing between the sensing electrode and the counter electrode is of the order of one millimeter and is not critical.

When the sensor is exposed to air or oxygen, oxygen gas permeates through the membrane and is reduced at the sensing electrode. At the same time, the counter copper electrode is oxidized to copper oxide. The resulting current flows through an external resistor network and produces a voltage which is read on a voltmeter.

Typically, at a temperature of 75° F., the resistor network has a resistance of 110 ohms. Exposure of the sensor to air at 1 atmosphere pressure produces a current of about 400 microamperes ($\mu A$) and an output voltage of 44 millivolts across the resistor network. If the exposed surface of the membrane and the resistance values of the resistor network and the concentration of oxygen in air at constant temperature to which the sensor is exposed are all maintained as provided in prior art devices as specified above, the life of the prior art sensor is about 8800 hours. A sensing circuit suitable for use in connection with a sensor as provided pursuant to the present invention is illustrated schematically in FIG. 3.

The circuit is connected to sensing electrode 122 and counter electrode 124 by the wires 130 and 132. These elements of the circuit appear in FIG. 1 under the numerals 22, 24, 30 and 32 respectively.

A voltmeter 140 is connected in series with the sensing electrode 122 and counter electrode 124 through the wires 130 and 132 and gives a reading in millivolts of the voltage developed between the two electrodes when oxygen is being reduced as sensing electrode 122. The current can be calibrated in terms of partial pressure of oxygen to which the exterior of membrane 20 of FIG. 1 is exposed as is conventional with oxygen sensors. However as pointed out above, for a prior art oxygen sensor as described here the device must be recalibrated continually inasmuch as the sensitivity of the device decreases with time. Some details of oxygen sensing equipment are described in the U.S. Pat. Nos. 3,149,921 and 3,616,411 which are incorporated herein by reference.

A thermistor/resistor network 144, enclosed by dashed lines in FIG. 3, is provided in parallel with a voltage meter 140 to permit a selected voltage to be developed between lines 130 and 132. The network consists of a variable resistor 146 in series with a thermistor 148, and a second variable resistor 150 in parallel with thermistor 148. The thermistor is incorporated in the known prior art circuit as illustrated to provide compensation for change in temperature of the sensor.

As indicated above for prior art sensors, typically at a temperature of 75° F., the resistor network has a resistance from line 130 to line 132 of 110 ohm. Output voltage is 44 millivolts on exposure of such prior art sensor to air at 1 atmosphere pressure and a current of about 400 microamperes is generated.

The prior art oxygen sensors as described above have been used for a number of years. Sensors as described above have been supplied to NASA for a period of over eight years.

When the sensitivity of these prior art sensors changes and recalibration and adjustment of the device is needed, adjustments are made to the variable resistors 146 and 150. In this way, and with timely recalibration of the devices, effective sensing of oxygen is feasible.

We have recently discovered that a conventional oxygen sensor such as that illustrated in FIG. 1 and described above and incorporating a conventional porous copper counter electrode had a deposit of copper oxide formed on the sensing electrode. We attribute the formation of the copper oxide deposit on the sensing electrode at least in part to the significant solubility of that portion of the copper counter electrode which has been oxidized to cupric oxide, CuO. We believe that the soluble copper oxide species can migrate and diffuse to the sensing electrode where they precipitate as an oxide deposit. Such deposit is believed to gradually and increasingly block the catalytic sites on the sensing electrode which are required for efficient oxygen reduction. The blocking of such catalytic sites results in a gradual decrease in the oxygen sensitivity of the sensor.

We also believe that the loss of sensitivity of conventional and prior art oxygen sensors is at least in part attributable to an internal swelling which occurs within the copper counter electrode as the dense copper of the electrode is converted to the less dense cuprous oxide, $Cu_2O$. The original 7.6 grams of copper may be oxidized completely to become 8.56 grams of $Cu_2O$. The original 7.6 grams of copper occupy 0.85 cubic centimeters. When fully oxidized to cuprous oxide the 0.85 cubic centimeters of copper becomes 1.43 cubic centimeters of the less dense $Cu_2O$. This requires an increase in volume of 68%. While some of the cuprous oxide does dissolve and migrate to the sensor electrode where it can create the problems discussed above, the increase of 68% of the volume of the copper in the counter electrode is believed to add to the development of a progressive inhibition of the oxidation reaction and accordingly a reduction in the sensitivity of the oxygen sensor.

While it is true that the copper counter electrode described above is approximately 65% porous the problem of the increasing volume of the material within the counter electrode as the dense copper metal is converted to the less dense cuprous oxide is deemed to at least partially inhibit and interfere with the oxidation of the electrode particularly at the latter stages of the total life of the oxygen sensor.

Figure 2:
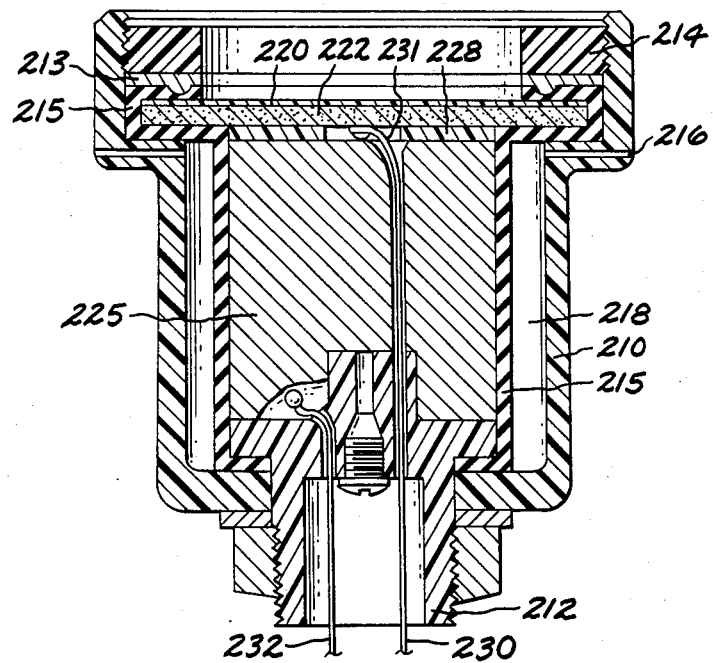
FIG. 2 is an axial sectional view of an oxygen sensor as provided pursuant to the present invention.

The oxygen sensor of the present invention is described now with reference to FIG. 2.

The structure of the device of FIG. 2 is similar in a number of respects to that of FIG. 1. Because of these similarities the reference numerals that are used in describing the structure are increased by the numeral 200 but are otherwise similar to the structures of the units with the unit numbers of FIG. 1.

However there are substantial differences and the description here concerns mainly the differences in the structure and the very significant advantages which result from the difference in structure which is provided. One quite important difference concerns the porous metal counter electrode 225. The counterpart in the device of FIG. 1 is the porous metal copper electrode 24. In the device of FIG. 2 the structure includes a porous metal counter electrode formed of cadmium.

A preferred cadmium porous counter electrode is one which is formed with the aid of a foam metal such as a nickel foam metal. Nickel foam metal is a commercially available product and has a porosity of over 90%. A porous cadmium counter electrode can be formed using a foam metal substructure, by depositing cadmium metal on and in the foam metal. For this purpose a solid substructure foam metal such as nickel foam is first machined to have the overall shape of the counter electrode 225 as illustrated in FIG. 2. Such a substructure may have about 5 to 10% by volume of foam nickel metal.

Using the shaped superstructure a porous cadmium electrode may be formed by a number of techniques using a combination of conventional technologies.

One technique involves introducing cadmium oxide into the nickel foam and reducing the cadmium oxide to cadmium metal. For this purpose a slurry of cadmium oxide in water or other liquid carrying medium is first introduced into the substructure. Once in place the slurry is dried to leave a coating of CdO on and in the foam nickel superstructure. The CdO is then reduced chemically to cadmium metal. The reduction to cadmium metal may be accomplished electrochemically or chemically as by chemical reduction using hydrogen gas.

Another way in which such a porous cadmium counter electrode may be formed is by electrochemical deposition of the cadmium metal from a plating bath onto and into the foam metal substructure. For this purpose the foam nickel counter electrode sub-structure is introduced into an electrolytic bath as of cadmium nitrate and made the cathode of an electrolytic cell. Cadmium is then plated onto the nickel substructure preferably in dendritic form to have a high surface area.

A further alternative is the electrodeposition of a cadmium hydroxide layer in the interstices of the foam metal substructure followed by the chemical reduction of the hydroxide to metal. The cadmium hydroxide deposit may be formed in an acidic electrolytic bath as for example a bath containing cadmium nitrate dissolved in weak nitric acid electrolyte. Cadmium hydroxide is precipitated from such a bath electrochemically and the cadmium hydroxide is then electrochemically reduced in place in the substructure as by an applied current hydrogen gas to form a porous cadmium counter electrode.

The individual steps of the procedures described here for forming a porous cadmium counter electrode are conventional processing steps and within the skill of those skilled in the relevant art. The product formed, specifically a porous cadmium counter electrode built in and on a foam metal substructure suitable for use in an oxygen sensor is a novel and unique article.

The cadmium metal counter electrode preferably has a relatively high porosity which in the preferred form is above 40% porosity and as high as 60 to 70% porosity. A cadmium counter electrode having a porosity of about 65% is highly desirable as will be evident from the description below. The operation of the structure of the device of FIG. 2 is similar to that of the device of FIG. 1 but there are important differences as also discussed below.

The operation of the device of FIG. 2 is as follows. Oxygen in an ambient atmosphere to be measured is brought into contact with the oxygen permeable membrane 220. Oxygen which diffuses through the membrane comes into contact with the sensor electrode 222. While in contact with the electrode 222 the oxygen is reduced by acceptance of electrons and becomes hydroxyl ion according to the following equation:

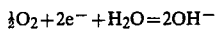
$$\tfrac{1}{2}O_2 + 2e^- + H_2O = 2OH^-$$

The hydroxyl ions are formed at the sensing electrode 222 by interaction of the oxygen with the electrons from the sensing electrode and with the water of the potassium hydroxide solution which wets the sensing electrode 222. After the hydroxyl ions are formed they can migrate through the sensing electrode 222 and past the insulating wafer 228 to enter the interstices of a cadmium counter electrode 225. The counter electrode is formed of cadmium which is in a porous state. The porous cadmium electrode has a porosity in the range of 40–70% and preferably above 60%. The hydroxyl ions at the sensing electrode 222 interact with the cadmium metal of the counter electrode 225 according to the following equation:

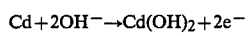
$$Cd + 2OH^- \rightarrow Cd(OH)_2 + 2e^-$$

On an overall basis the oxygen which enters the sensor through the permeable membrane 220 becomes associated with the cadmium as the hydroxide with the aid of a single molecule of water for each oxygen atom which enters the sensor. On an overall basis the equation is as follows:

$$Cd + \tfrac{1}{2}O_2 + H_2O \rightarrow Cd(OH)_2$$

On an overall basis the current generated in the cell flows through the wires 230 and 232 through an external network such as that of FIG. 3. The values of the resistances of the network are different from those used with reference to the cell of FIG. 1. However in the operation of the cell of FIG. 2 with a network as illustrated in FIG. 3 there is far less need to adjust the values of the variable resistances although it is deemed desirable to retain the ability to adjust the resistance values in a cadmium-based oxygen sensor.

The sensitivity of a cadmium-based oxygen sensor decreases considerably less with time than the sensitivity of a prior art of even of a state of the art copper-based oxygen sensor. This beneficial lessening of sensitivity decrease is believed to result principally from the fact that cadmium hydroxide has significantly lower solubility in an electrolyte such as a potassium hydroxide electrolyte of an oxygen sensor cell than cupric oxide. It is believed to be the relatively high solubility of cupric oxide in potassium hydroxide coupled with the tendency of the cupric oxide to deposit as a solid on the sensing electrode and to coat and block the catalytic sites of the sensing electrode that causes the deleterious reduction in sensitivity of oxygen sensing cells which incorporate the conventional porous copper counter electrode.

Because there is substantially lower cadmium solubility in the electrolyte there is less diffusion and migration of cadmium ion species within the cell. Accordingly there is less cadmium ion species such as cadmium hydroxide to migrate to and to precipitate at the sensing electrode of the cell as solid cadmium hydroxide. As a consequence the blocking of catalytic sites for oxygen reduction is much less pronounced and the decrease of the oxygen sensitivity of a cell with a porous cadmium electrode is much slower. Such reduced loss of sensitivity is a distinct advantage in the operation and use of an oxygen sensor cell as for example in a space craft.

Because the water of the electrolyte becomes bound into the cadmium hydroxide as hydroxyl or hydroxide there is a gradual depletion of water from the alkaline electrolyte solution and accordingly a gradual increase of the concentration of the alkalinity of the alkaline electrolyte, especially next to the sensing electrode. This leads to less precipitation of cadmium hydroxide. We deem this to be desirable in the operation of an oxygen sensor cell and believe that the increase in the alkalinity of the sensor electrolyte over a period of time can have the effect of maintaining the sensitivity of the cell in its ability to sense oxygen and assisting in overcoming the problem of a sensitivity which declines with time.

An initial concentration of alkaline electrolyte may be, for example in the case of a device as illustrated in FIG. 2, about 34% KOH. The concentration of the KOH in the cell will gradually increase during the life of the battery.

The following description of the quantities and volumes of electrolyte is given independently of the foam metal substructure as the substructure itself is low volume and is essentially inert in the operation of the cell.

For a cell as illustrated in FIG. 2 an initial volume of electrolyte of about 4.73 cubic centimeters may be used. This volume of electrolyte is approximately twice the volume of electrolyte which is employed in a conventional cell as illustrated in FIG. 1 containing a copper counter electrode capable of generating the same number of ampere hours as that generated in the device of FIG. 2.

As indicated above approximately 7.6 grams of copper are employed in the prior art cell as described with reference to FIG. 1. This quantity of copper produces about 3.2 ampere hours of electricity over the life of the battery. A mass of 6.7 grams of cadmium is needed to produce about the same amount of electricity, namely about 3.2 ampere hours.

The 6.7 grams of cadmium will generate 8.21 grams of cadmium hydroxide if the cadmium is converted entirely to cadmium hydroxide in the operation of the sensor cell. The density of cadmium hydroxide is approximately 4.8 grams per cubic centimeter and the complete conversion of the cadmium to cadmium hydroxide will result in formation of approximately 1.71 cubic centimeters of cadmium hydroxide in the cell. The amount of water which is extracted from the electrolyte by such conversion of 6.7 grams of cadmium completely to cadmium hydroxide is about 1.07 cubic centimeters. This corresponds to about 1.07 grams of water of the electrolyte.

A preferred form of the cell is one in which the volume of porous cadmium is about 4.49 cubic centimeters. The net density of the porous cadmium counter electrode is approximately 30% and its porosity is accordingly about 70%. A cadmium counter electrode for a cell as illustrated in FIG. 2 would be a cylinder approximately 1.8 centimeters in diameter and 2.0 centimeters long as contrasted with the copper counter electrode of the device of FIG. 1 which was 1.2 centimeters long. A center bore of the device of FIG. 1 was approximately 0.8 centimeters in diameter whereas the bore of the device of FIG. 2 is approximately 0.2 centimeters. The device of FIG. 1 contained about 2.2 cubic centimeters of electrolyte and the device of FIG. 2 contains about 4.3 cubic centimeters of electrolyte or about double that of the device of FIG. 1.

Another advantage of the device of FIG. 2 is that it has a small "swell factor". By this is meant that the increase in total volume in the cell is much lower than that occurring in the prior art device of FIG. 1. This is partly because as the volume of $Cd(OH)_2$ increases the volume of $H_2O$ decreases. The 6.7 grams of dense cadmium metal originally occupy 0.77 cc of the cell. This volume is increased to 1.71 cc when the dense cadmium is converted completely to $CD(OH)_2$. However the water volume in the cell is simultaneously reduced by 1.07 cc. Accordingly the increase in solids volume in the cell is essentially completely offset by the decrease in liquid volume.

While the solids volume increases from 0.77 cc to 1.71 cc or an increase of 0.94 cc the volume of liquid in the cell decreases by 1.07 cc. Because the increase in solids volume is thus essentially completely offset by the decrease in liquids volume there is essentially no overall swelling effect during the entire operating life of the cell as the cadmium metal is completely converted to cadmium hydroxide.

The device of this invention as illustrated in FIG. 2 may be preconditioned by forming a cadmium hydroxide layer on the cadmium of the counter electrode 225. The formation of such surface layer having a plurality of layers of cadmium hydroxide on the cadmium metal of the counter electrode results in the conditioning of the cell so that some of the break-in time required for portable prior art oxygen sensors may be eliminated. Such break-in time activity involves bringing the cell up to a level of operation where reliable readings can be taken as explained more fully in the application for patent of the same inventors filed simultaneously herewith Ser. No. 665,672, filed Oct. 29, 1984, the text of which is incorporated herein by reference.

As also explained above an important advantage of the device of the present invention is that the cadmium hydroxide which is formed in the alkaline electrolyte is highly insoluble. Its insolubility results in its remaining in place in the counter electrode and avoids the problem of a soluble compound diffusing from the counter electrode to the sensing electrode and precipitating out at the sensing electrode to cut down on the sensitivity of the sensing electrode. The solubility of cadmium hydroxide in the environment of the cell of FIG. 2 as described above is substantially lower than the solubility of cupric oxide in the cell of FIG. 1 as also described above.

What is claimed and sought to be protected by Letters Patent of the United States is as follows:

1. An oxygen sensor of improved stable sensitivity which comprises
    a sensor electrode adapted to reduce oxygen which permeates thereto through a diffusion barrier,
    a counter electrode of porous cadmium metal formed on a support structure of nickel foam metal
    a set of conductors and a thermistor/resistor network providing a series electric connection between said electrodes and a voltmeter in parallel with said network and providing indication of oxygen level by calibrated readings of said voltmeter, and
    an aqueous alkaline solution providing an electrolytic path between said electrodes.

2. A portable sensor of claim 1 in which the weight of cadmium is less than 10 grams.

3. A portable sensor of claim 1 in which the cadmium has a porosity of greater than 40%.

4. The portable sensor of claim 1 in which the porosity of the cadmium electrode is greater than 60%.

5. A method of forming a stable and reliable oxygen sensor which comprises
    providing means for diffusion of oxygen gas from an atmosphere to be sensed through a permeable membrane to a sensor electrode,
    providing an oxygen sensor cell including said sensing electrode and a porous cadmium counter electrode formed on a support structure of foam nickel,
    electrically connecting said electrodes through a resistor circuit and a voltmeter,
    conditioning said counter electrode by forming cadmium hydroxide layer on the surface of said porous cadmium electrode, and
    establishing an electrolytic path between said counter electrode and said sensing electrode through an alkaline electrolyte.

6. The method of claim 5 in which the electrolytic path is established through potassium hydroxide solution.

7. The method of claim 5 wherein the voltmeter is calibrated to give readings in partial pressure of oxygen in said atmosphere.

8. The method of claim 5 in which the cadmium counter electrode is over 60% porous.

* * * * *